(12) United States Patent
Nelis

(10) Patent No.: US 12,048,621 B2
(45) Date of Patent: Jul. 30, 2024

(54) ENDOPROSTHESIS

(71) Applicant: VASCUTEK LIMITED, Renfrewshire (GB)

(72) Inventor: Vincent Nelis, Renfrewshire (GB)

(73) Assignee: VASCUTEK LIMITED, Renfrewshire (GB)

( * ) Notice: Subject to any disclaimer, the term of this patent is extended or adjusted under 35 U.S.C. 154(b) by 0 days.

(21) Appl. No.: 16/595,911

(22) Filed: Oct. 8, 2019

(65) Prior Publication Data

US 2020/0038169 A1 Feb. 6, 2020

Related U.S. Application Data

(63) Continuation of application No. PCT/GB2018/051127, filed on Apr. 27, 2018.

(30) Foreign Application Priority Data

May 2, 2017 (GB) ...................................... 1706976

(51) Int. Cl.
*A61F 2/07* (2013.01)

(52) U.S. Cl.
CPC .......... *A61F 2/07* (2013.01); *A61F 2002/075* (2013.01); *A61F 2210/0014* (2013.01);
(Continued)

(58) Field of Classification Search
CPC .................. A61F 2/07; A61F 2002/075; A61F 2210/0014; A61F 2220/005;
(Continued)

(56) References Cited

U.S. PATENT DOCUMENTS

| | | |
|---|---|---|
| 4,580,568 A | 4/1986 | Gianturco |
| 5,290,305 A | 3/1994 | Inoue |

(Continued)

FOREIGN PATENT DOCUMENTS

| | | |
|---|---|---|
| CA | 2872125 A1 | 4/2011 |
| EP | 0855171 A2 | 7/1998 |

(Continued)

OTHER PUBLICATIONS

International Search Report and Written Opinion of the International Searching Authority for International Application No. PCT/GB2018/051127 mailed on Jul. 10, 2018.
(Continued)

*Primary Examiner* — Megan Y Wolf
(74) *Attorney, Agent, or Firm* — Stephen J. Kenny; Foley Hoag LLP

(57) ABSTRACT

A stent graft prosthesis includes a fabric sleeve supported by a series of ring stents, including ring stents having a saddle shape with peaks and valleys, the axial alignment of equivalently shaped ring stents in the series of ring stents being such that with respect to at least one shaped ring stent other shaped ring stents are angularly offset. Multiple series of ring stents may be interposed such that at least one ring stent in a first series of ring stents $S_1$-$S_n$ is located between two ring stents in at least one other series of ring stents $S°_1$-$S°_n$, the angular offset of ring stents in the first series $S_1$-$S_n$ being different from the angular offset of ring stents in at least one other series of ring stents ($S°_1$-$S°_n$). The offset changes the amount of fabric surface between peripheral contact points of successive shaped ring stents.

14 Claims, 14 Drawing Sheets

(52) U.S. Cl.
CPC . *A61F 2220/005* (2013.01); *A61F 2220/0058* (2013.01); *A61F 2220/0075* (2013.01); *A61F 2230/0095* (2013.01)

(58) Field of Classification Search
CPC ...... A61F 2220/0058; A61F 2220/0075; A61F 2230/0095; A61F 2/853; A61F 2002/826
See application file for complete search history.

(56) References Cited

U.S. PATENT DOCUMENTS

| | | | |
|---|---|---|---|
| 5,578,072 | A | 11/1996 | Barone et al. |
| 5,591,228 | A | 1/1997 | Edoga |
| 5,824,041 | A * | 10/1998 | Lenker ............ A61F 2/91 606/195 |
| 5,925,074 | A | 7/1999 | Gingras et al. |
| 6,036,723 | A | 3/2000 | Anidjar et al. |
| 6,203,568 | B1 | 3/2001 | Lombardi et al. |
| 6,635,080 | B1 | 10/2003 | Lauterjung et al. |
| 6,673,103 | B1 | 1/2004 | Golds et al. |
| 6,773,457 | B2 | 8/2004 | Ivancev et al. |
| 6,938,646 | B2 | 9/2005 | Litton |
| 7,780,622 | B2 | 8/2010 | Fitzpatrick et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,652,198 | B2 | 2/2014 | Andreas et al. |
| 8,740,971 | B2 | 6/2014 | Iannelli |
| 8,968,389 | B2 | 3/2015 | Greenberg et al. |
| 9,056,002 | B2 | 6/2015 | Tabor |
| 9,398,964 | B2 | 7/2016 | McGee et al. |
| 9,510,936 | B2 | 12/2016 | McDonald et al. |
| 9,622,894 | B2 | 4/2017 | McGee |
| 9,788,983 | B2 | 10/2017 | Johnson et al. |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 10,413,396 | B2 | 9/2019 | Ashton |
| 10,724,805 | B2 | 7/2020 | Barmeier et al. |
| 11,026,823 | B2 | 6/2021 | McDonald et al. |
| 11,458,008 | B2 | 10/2022 | Debus et al. |
| 11,471,261 | B2 | 10/2022 | McDonald |
| 11,554,033 | B2 | 1/2023 | Kolbel et al. |
| 2003/0024527 | A1 | 2/2003 | Ginn |
| 2003/0120263 | A1 | 6/2003 | Ouriel et al. |
| 2003/0130720 | A1 | 7/2003 | DePalma et al. |
| 2003/0135257 | A1 | 7/2003 | Taheri |
| 2003/0176911 | A1 | 9/2003 | Iancea et al. |
| 2004/0117003 | A1 | 6/2004 | Ouriel et al. |
| 2004/0167618 | A1 | 8/2004 | Shaolian et al. |
| 2004/0215315 | A1 | 10/2004 | Jones et al. |
| 2004/0243221 | A1 * | 12/2004 | Fawzi ............ A61F 2/07 623/1.36 |
| 2005/0033399 | A1 * | 2/2005 | Richter ............ A61F 2/91 623/1.11 |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2006/0184226 | A1 | 8/2006 | Austin |
| 2006/0229700 | A1 | 10/2006 | Acosta et al. |
| 2007/0010873 | A1 | 1/2007 | Neri |
| 2007/0055347 | A1 | 3/2007 | Arbefeuille |
| 2007/0106368 | A1 | 5/2007 | Vonderwalde |
| 2007/0112422 | A1 | 5/2007 | Dehdashtian |
| 2007/0135904 | A1 | 6/2007 | Eidenschink et al. |
| 2007/0168013 | A1 | 7/2007 | Douglas |
| 2007/0208409 | A1 | 9/2007 | Quigley |
| 2008/0082159 | A1 | 4/2008 | Tseng et al. |
| 2008/0147171 | A1 | 6/2008 | Ashton et al. |
| 2008/0188924 | A1 | 8/2008 | Prabhu |
| 2009/0043330 | A1 | 2/2009 | To |
| 2009/0264991 | A1 | 10/2009 | Paul, Jr. et al. |
| 2010/0152835 | A1 | 6/2010 | Orr |
| 2010/0222869 | A1 | 9/2010 | Delaney |
| 2010/0234937 | A1 | 9/2010 | Wang et al. |
| 2011/0054586 | A1 | 3/2011 | Mayberry et al. |
| 2011/0066221 | A1 * | 3/2011 | White ............ A61F 2/07 623/1.11 |
| 2011/0190862 | A1 | 8/2011 | Bashiri et al. |
| 2011/0230956 | A1 | 9/2011 | White |
| 2012/0059448 | A1 | 3/2012 | Parker et al. |
| 2012/0071960 | A1 | 3/2012 | Tani |
| 2012/0136431 | A1 | 5/2012 | Chen |
| 2012/0158121 | A1 | 6/2012 | Ivancev et al. |
| 2012/0172887 | A1 | 7/2012 | Hatfield |
| 2012/0239136 | A1 * | 9/2012 | Bruzzi ............ A61F 2/90 623/1.16 |
| 2012/0271401 | A1 * | 10/2012 | Bruszewski ............ A61F 2/966 623/1.15 |
| 2012/0277849 | A1 | 11/2012 | Tani et al. |
| 2012/0290068 | A1 | 11/2012 | Roeder et al. |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289700 | A1 | 10/2013 | Acosta-Acevedo |
| 2013/0289713 | A1 | 10/2013 | Pearson et al. |
| 2014/0005586 | A1 | 1/2014 | Feinstein |
| 2014/0121761 | A1 * | 5/2014 | McDonald ............ A61F 2/07 623/1.16 |
| 2014/0194970 | A1 | 7/2014 | Chobotov |
| 2014/0200648 | A1 | 7/2014 | Newell et al. |
| 2014/0249617 | A1 | 9/2014 | Argentine et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1 | 4/2015 | Becking et al. |
| 2015/0190221 | A1 | 7/2015 | Schaefer et al. |
| 2015/0257910 | A1 | 9/2015 | Duong et al. |
| 2015/0265444 | A1 | 9/2015 | Kitaoka |
| 2016/0175132 | A1 | 6/2016 | Wilger et al. |
| 2017/0014221 | A1 * | 1/2017 | Kelly ............ A61F 2/89 |
| 2018/0228593 | A1 * | 8/2018 | Eaton ............ A61F 2/07 |
| 2019/0192273 | A1 | 6/2019 | Debus et al. |
| 2019/0223996 | A1 | 7/2019 | McDonald |
| 2020/0038184 | A1 | 2/2020 | McLean |
| 2020/0038211 | A1 | 2/2020 | Kolbel et al. |
| 2020/0214821 | A1 | 7/2020 | McDonald |
| 2021/0204954 | A1 | 7/2021 | Nimmo |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0299424 | A1 | 9/2021 | King |
| 2021/0307641 | A1 | 10/2021 | Rumbles et al. |
| 2022/0023080 | A1 | 1/2022 | McDonald |
| 2022/0023081 | A1 | 1/2022 | McDonald |
| 2022/0273415 | A1 | 9/2022 | Brodie et al. |
| 2022/0378569 | A1 | 12/2022 | McDonald |
| 2023/0015592 | A1 | 1/2023 | Debus et al. |
| 2023/0119898 | A1 | 4/2023 | Kölbel et al. |
| 2023/0225853 | A1 | 7/2023 | Zeitani et al. |

FOREIGN PATENT DOCUMENTS

| | | |
|---|---|---|
| EP | 0880979 A1 | 12/1998 |
| EP | 1736116 A2 | 12/2006 |
| EP | 1847236 A2 | 10/2007 |
| EP | 2606852 A1 | 6/2013 |
| EP | 2676639 A1 | 12/2013 |
| EP | 3115022 A1 | 1/2017 |
| EP | 3248572 A1 | 11/2017 |
| EP | 3323385 A1 | 5/2018 |
| GB | 2491477 A | 12/2012 |
| GB | 2517689 A | 3/2015 |
| JP | H07308330 A | 11/1995 |
| JP | 2017042236 A | 3/2017 |
| RU | 2720745 C1 | 5/2020 |
| WO | WO-03/035130 A1 | 5/2003 |

(56) References Cited

FOREIGN PATENT DOCUMENTS

| WO | WO-2004/017866 A1 | 3/2004 |
|---|---|---|
| WO | WO-2004/064686 A1 | 8/2004 |
| WO | WO-2006/019626 A2 | 2/2006 |
| WO | WO-2006/034340 A1 | 3/2006 |
| WO | WO-2006/088638 A1 | 8/2006 |
| WO | WO-2008/057569 A1 | 5/2008 |
| WO | WO-2008/088835 A1 | 7/2008 |
| WO | WO-2008/112270 A1 | 9/2008 |
| WO | WO-2009/009376 A2 | 1/2009 |
| WO | WO-2009/082718 A1 | 7/2009 |
| WO | WO-2009/153768 A1 | 12/2009 |
| WO | 2010053563 A1 | 5/2010 |
| WO | WO-2012/043011 A1 | 4/2012 |
| WO | 2012164292 A1 | 12/2012 |
| WO | WO-2013/152327 A1 | 10/2013 |
| WO | WO-2014/096811 A2 | 6/2014 |
| WO | WO-2014/163957 A1 | 10/2014 |
| WO | WO-2016/054537 A1 | 4/2016 |
| WO | WO-2016075615 A2 | 5/2016 |
| WO | WO-2017/136733 A1 | 8/2017 |
| WO | WO-2017/203056 A1 | 11/2017 |
| WO | WO-2018/156848 A1 | 8/2018 |

OTHER PUBLICATIONS

Parodi, J.C., et al., "Transfemoral Intraluminal Graft Implantation for Abdominal Aortic Aneurysms", Annals of Vascular Surgery, vol. 5, pp. 491-499 (1991).
United Kingdom Search Report for GB Application No. 1706976.6 dated Jun. 22, 2021.
Levack et al., "Rapid Aortic Arch Debranching Using the Gore Hybrid Vascular Graft," Ann Thorac Surg, 95: e163-e165 (2013).
Nigro et al., "Use of the Gore Hybrid Vascular Graft in a challenging high-lying extracranial carotid artery aneurysm," J Vasc Surg, 59: 817-820 (2014).
Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).
European Search Report issued in European Patent Application No. 17767890.1, Jul. 28, 2020, 7 pages.
International Preliminary Report on Patentability for Application No. PCT/GB2021/052337 dated Mar. 23, 2023.
International Search Report and Written Opinion of the International Searching Authority for International Application No. PCT/GB2017/052602 mailed on Jan. 9, 2018.

\* cited by examiner

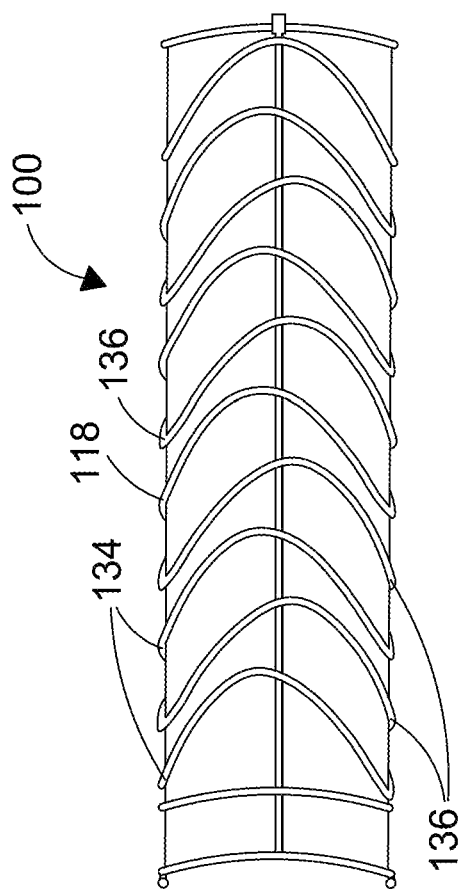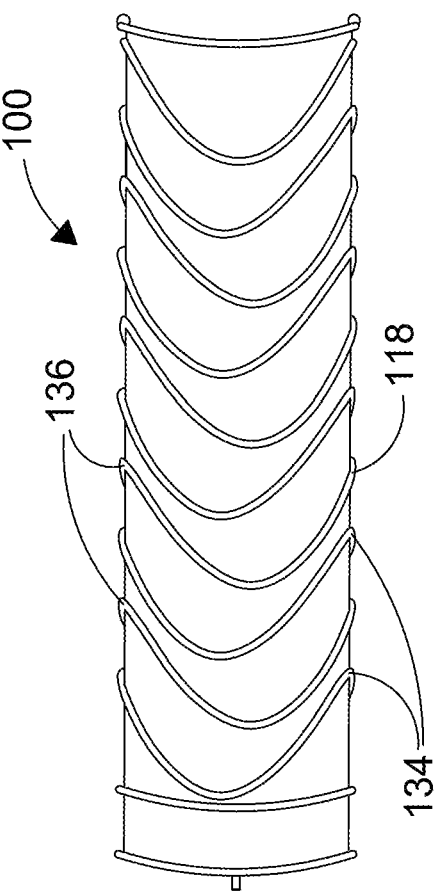

ENDOPROSTHESIS

CROSS REFERENCE TO RELATED APPLICATIONS

This application is claims priority benefit from International Application No. PCT/GB2018/051127, filed on Apr. 27, 2018, which claims priority to Great Britain Patent Application No. 1706976.6, filed on May 2, 2017, each of which is incorporated herein by reference in its entirety.

FIELD OF THE INVENTION

This invention relates to medical devices, particularly prosthetic implants or grafts incorporating tubular sleeves supported at least in part by ring stents. An endoprosthesis is disclosed herein which is suitable for implantation within the lumen of a natural vessel which requires treatment to compensate for damage or the consequences of aging or disease. The natural vessel may be part of the vasculature.

BACKGROUND OF THE INVENTION

Artificial prostheses consisting of a tubular conduit having an open lumen are well-known and are used in medicine to replace diseased or damaged natural body lumens, such as, for example, blood vessels or other hollow organs for example bile ducts, sections of intestine or the like. The most common use of such artificial prostheses is to replace diseased or damaged blood vessels.

A number of vascular disorders can be treated by use of an artificial prosthesis. One relatively common vascular disorder is an aneurysm. Aneurysm occurs when a section of natural blood vessel wall, typically of the aortic artery, dilates and balloons outwardly. Whilst small aneurysms cause little or no symptoms, larger aneurysms pose significant danger to a patient. Rupture of an aortic aneurysm can occur without warning and is usually fatal, so significant emphasis is placed on early diagnosis and treatment. With an increasing ageing population, the incidence of aneurysm continues to rise in western societies.

Provided that an aneurysm is diagnosed prior to rupture, surgical treatment to repair the affected vessel wall is effective. Surgical treatment of an aortic aneurysm for example, involves the replacement or reinforcement of the aneurismal section of aorta with a synthetic graft or prostheses under general anaesthesia allowing the patient's abdomen or thorax to be opened (see Parodi et al., Annals of Vascular Surgery (1991) 5:491-499). The patient will then have a normal life expectancy.

Surgical repair of aneurysm is however a major and invasive undertaking and there has been much effort in developing less invasive methods. Currently, aneurysm repair generally involves the delivery by catheter of a fabric or ePTFE graft which is retained at the required location by deployment of metallic stent elements. The preferred procedure is generally based upon the long established Seldinger (guide wire) technique. The ability to deliver the graft/stent device by catheter reduces the surgical intervention to a small cut-down to expose the femoral artery and, in suitable circumstances, the device can be deployed percutaneously. Catheter delivery is beneficial since the reduced invasive nature of the procedure allows utilisation of a local anaesthetic and leads to reduced mortality and morbidity, as well as decreased recovery time. For example, endovascular repair is typically used for repair of infra-renal abdominal aortic aneurysms where the graft is placed below the renal arteries. Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

However, whilst the endovascular repair of aneurysms is now accepted as the method of choice, the technique has significant limitations and is not suitable for all patients.

As mentioned above, other vascular disorders are treatable by use of a vascular prosthesis. Examples include (but not limited to) occlusions, stenosis, vascular damage due to accident or trauma, and the like. Vascular prostheses are also used in by-pass techniques.

A stent graft prosthesis may be used in other natural vessels to restore or open up a lumen occluded or otherwise restricted by damage or disease. Thus the stent graft prosthesis disclosed hereinbelow may be used for repair to other hollow organs such as bile ducts, sections of intestine, etc.

Endovascular techniques involve the delivery of a prostheses by catheter. Since the internal lumen of the catheter defines the maximum dimensions of the prostheses to be inserted, much effort has been expended in the design of prostheses which can be packaged in a minimal volume, and are easy to deploy once positioned at the required location.

One successful type of prosthesis, is a stent graft comprising a conduit formed from a flexible sleeve attached to a rigid support or stent. The sleeve will typically be made of a fabric (usually a knitted or woven fabric) of ePTFE, PTFE or polyester, polyethylene or polypropylene and may optionally be coated to reduce friction; discourage clotting or to deliver a pharmaceutical agent. The fabric will generally be porous on at least one surface to enable cell in-growth. The stent may be balloon-expandable (e.g. a PALMAZ stent made of rigid stainless steel wire), but could also be self-expandable and formed of a shape memory material, such as nitinol (a nickel-titanium alloy). Numerous different stent designs are known in the art, for example braided stents as described in EP 880979 or wire zig-zag stents as described in U.S. Pat. No. 4,580,568.

Stent grafts are commonly formed with a plurality of stents spaced along the graft. WO 2010/053563 describes a stent graft designed for deployment in a curved vessel. Identical zig-zag rings or Z-stents are spaced further apart from each other in the region of the stent graft which undergoes the greatest curvature. Thus, the inter-stent spacing varies along at least part of length of the graft. However, for treatment of aneurysm, it is desirable that the stent graft exhibits a degree of stiffness across the diseased (aneurismitic) portion of the blood vessel under repair.

Stent grafts having such unconnected stent elements have the disadvantage that the rings lack stability, and in particular the rings have a tendency to rotate or tilt relative to each other either during deployment or following deployment. Improvements in stent grafts are disclosed in WO 2012/164292A1 which address such tilting disadvantages.

Stent grafts having such discrete ring stents may be susceptible to ring stent axial displacement with respect to the longitudinal axis of the stent graft, such that undesirable compression or extension of at least parts of the stent graft may occur when the stent graft is being positioned and deployed within a lumen.

SUMMARY OF THE INVENTION

A stent graft prosthesis as disclosed herein, comprising a fabric sleeve supported by a series of ring stents, several of which ring stents have an undulating shape, offers improved strength characteristics in the overall structure by changing the axial alignment of equivalently shaped ring stents in the series of ring stents such that with respect to at least one of these shaped ring stents other shaped ring stents are angularly offset. This is advantageous because the offset arrangement changes the amount of fabric surface between selected peripheral contact points of successive ones of the shaped ring stents in the series of ring stents.

A stent graft prosthesis may comprise:
  a tubular member having a length dimension L extending between a first end of the tubular member and a second end of the tubular member, and a lumen width dimension W; and
  a plurality of discrete compressible ring stents spaced apart and attached along the length of the tubular member, each compressible ring stent having an undulating contour forming a plurality of alternate peaks and valleys, and a height dimension H, each compressible ring stent extending around and attached to an external surface or an internal surface of the tubular member in a direction non-parallel to the length of the tubular member,
  wherein the peaks and valleys of at least one compressible ring stent are offset angularly with respect to the peaks and valleys of an adjacent compressible ring stent.

In such a stent graft prosthesis, according to this disclosure, a ring stent may be rotationally displaced with respect to an neighbouring unconnected ring stent by an angular offset in the range of 5 to 60 degrees.

Embodiments of ring stent-supported grafts are disclosed herein wherein multiple ring stents of similar shape and having an undulating contour forming a plurality of alternate "peaks" and "valleys" (saddle shaped stents) are mutually spaced apart and attached along the length of a tubular form graft and configured such that angular offset of a ring stent with respect to a neighbouring or adjacent ring stent offers improved strength in the graft in the region of the offset ring stents such that the said region exhibits column stiffness, yet the graft is still compressible sufficiently to be compactly packaged inside a removable sheath for delivery purposes using an appropriate delivery system.

In this disclosure, "axially" is used with reference to the longitudinal axis of a tubular form graft unless otherwise stated.

In this disclosure "angular offset" is a rotational displacement about the longitudinal axis of a tubular form graft and refers to comparison of a selected point at a radial position on a ring stent contour with a point at an equivalent radial position on a different ring stent which lies at a different axial location. In this way the orientation of the respective ring stents can be compared by reference to the amount of rotational displacement from a correspondingly aligned position to an offset position.

In this disclosure, "graft" is used in relation to a tubular member or body, typically a fabric sleeve which may be crimped or uncrimped, and requiring support from stents to maintain an open lumen therethrough. Radiopaque markers may be attached periodically to the fabric along the length of the tubular member.

For the avoidance of any doubt, a cross-section of the tubular member may be any hollow shape, for example, a hollow ellipsoid or a hollow circle.

In this disclosure "stent graft prosthesis" is used in relation to a "graft" that is supported by stents and configured for implantation into a natural vessel of the human or animal body.

In this disclosure, the term "saddle shaped" refers to a circular ring stent formed of a material which is sufficiently resilient to be distorted so that a first pair of diametrically opposed points on the circumference of the ring are displaced in one axial direction whilst a second pair of diametrically opposed points, centrally located on the circumference between the first pair, are displaced in the opposing axial direction to form a symmetrical saddle shape. For convenience, the first pair of points can be described as "peaks", with the second pair of points described as "valleys". The degree of axial displacement between the first pair of points and the second pair of points (which axial displacement is also termed the "saddle height"), is a function of the original circumference of the ring stent prior to its distortion, relative to the final circumference of a circle within which the distorted (saddle shaped) configuration can be located. Thus, the ratio of final circumference: original circumference provides a simplistic notation of the axial displacement. Generally the final circumference will be the outer circumference of the graft sleeve to which the stent is to be attached. The percentage oversize of the undistorted inner circumference of the circular stent relative to the outer circumference of the graft sleeve also gives a convenient measure of the saddle shape adopted, and can be calculated as:

$$\text{Oversize \%} = \frac{[\text{Stent inner diameter} - \text{Graft sleeve outer diameter}]}{\text{Graft sleeve outer diameter}} \times 100\%$$

In embodiments, ring stent-supported grafts may comprise multiple ring stents of similar shape and having an undulating contour forming a plurality of alternate "peaks" and "valleys" are mutually spaced apart and attached along the length of a tubular form graft, together with conventional "circular" ring stents located at one or both ends of the tubular form graft. In such embodiments, the ring stents at one or both ends of the tubular form graft may be provided with loop eyelets for securing the tubular form graft to tissue.

In embodiments, ring stent-supported grafts may comprise multiple ring stents of similar shape and having an undulating contour forming a plurality of alternate "peaks" and "valleys" are mutually spaced apart and attached along the length of a tubular form graft, and arranged in distinct series wherein a sub-set of the multiple ring stents are aligned with others in that sub-set to serve as a first oriented stent element and another sub-set of multiple ring stents are aligned with others in that sub-set to serve as a second oriented stent element, the orientation being such that the second oriented stent element is angularly offset with respect to the first oriented stent element.

In at least some embodiments the angular offset of one ring stent with respect to an adjacent ring stent may be such that in a series of successively offset ring stents, each being offset by the same angular amount, a notional line passing through a selected point on say a peak of a ring stent to an equivalent point on a peak of each of the successively offset ring stents would follow a spiral path around the graft.

An advantage of the offset arrangement is that the distance on a surface of the tubular form graft between supporting adjacent ring stents varies such that certain points are closer together than others which tends to inhibit undesirable compression or extension of at least parts of the stent graft with respect to the longitudinal axis of the tubular form graft. The angular offset may be such as to create a triangulation of the material making up the tubular form graft between certain points of the undulating contours of adjacent offset ring stents. It is observed that in such embodiments, material between a point on a peak of one ring stent and the axially closest point on the next ring stent is less than would be the case if these ring stents were not angularly offset, i.e. if these ring stents were axially aligned, peak to peak, valley to valley.

In at least some embodiments, the direction of angular offset of one ring stent with respect to an adjacent ring stent may be sequentially alternated, i.e. polarity reversed such that in a series of similarly shaped ring stents arranged along the longitudinal axis of a tubular member the angular offset is zero for the first stent ($S_1$), $+\theta$ for the next stent ($S_2$), $-\theta$ for the next stent ($S_3$), $+\theta$ for the next stent ($S_4$), $-\theta$ for the next stent ($S_5$), and so on. In such embodiments, two series $S^{a1}$ of ring stents ($S_1$-$S_n$) and $S^{a2}$ of ring stents ($S^{a2}_1$-$S^{a2}_n$) are formed wherein one series $S^{a2}$ of ring stents is angularly offset (rotated) with respect to the other series $S^{a1}$ of ring stents when viewed along the longitudinal axis.

A stent graft prosthesis may comprise several compressible ring stents, each compressible ring stent having an undulating contour forming a plurality of alternate peaks and valleys which has a height dimension H in the range of 2 to 30 mm said height dimension being a distance measured along a longitudinal axis aligned with the length of the tubular member and determined by measurement between ring stent peaks and ring stent valleys of a ring stent.

The plurality of ring stents may be configured as a series of ring stents spaced apart and attached along the length of the tubular member, and wherein with respect to a first ring stent having peaks and valleys in the series of ring stents, the next adjacent ring stent in the series has peaks and valleys which are offset angularly with respect to the peaks and valleys of the first ring stent, and the peaks and valleys of each successive ring stent in the series are offset angularly with respect to the peaks and valleys of the preceding adjacent ring stent.

Alternatively, the plurality of ring stents may be configured as a series of ring stents spaced apart and attached along the length of the tubular member, and wherein with respect to a first ring stent having peaks and valleys in the series of ring stents, a subsequent ring stent in the series of ring stents not being adjacent to the first ring stent has peaks and valleys which are offset angularly with respect to the peaks and valleys of the first ring stent.

Alternatively, the plurality of ring stents may be configured as a series of ring stents spaced apart and attached along the length of the tubular member, and wherein with respect to a ring stent having peaks and valleys within the series of ring stents, the next adjacent ring stent in the series has peaks and valleys which are offset angularly with respect to the peaks and valleys of the ring stent having peaks and valleys within the series of ring stents.

Alternatively, as can be seen in FIG. 18, the plurality of compressible ring stents spaced apart and attached along the length of the tubular member may be configured as at least a first series of compressible ring stents ($S_1$-$S_n$) and at least one other series of compressible ring stents ($S^o_1$-$S^o_n$), interposed such that at least one compressible ring stent in the first series of compressible ring stents ($S_1$-$S_n$) is located between two ring stents in the at least one other series of compressible ring stents ($S^o_1$-$S^o_n$), and wherein with respect to a first compressible ring stent ($S_1$) having peaks and valleys in the first series of compressible ring stents ($S_1$-$S_n$), the next compressible ring stent ($S_2$) in the first series ($S_1$-$S_n$) has peaks and valleys which are offset angularly (AO) with respect to the peaks and valleys of the first compressible ring stent ($S_1$) in the first series ($S_1$-$S_n$), and wherein with respect to a first compressible ring stent ($S^o_1$) in the at least one other series ($S^o_1$-$S^o_n$) the next compressible ring stent ($S^o_n$) in the at least one other series ($S^o_1$-$S^o_n$) has peaks and valleys of which are offset angularly ($AO^o$) with respect to the peaks and valleys of the first compressible ring stent ($S^o_1$) in the at least one other series ($S^o_1$-$S^o_n$), the angular offset (AO) of compressible ring stents in the first series ($S_1$-$S_n$) being different from the angular offset ($AO^o$) of compressible ring stents in the at least one other series of compressible ring stents ($S^o_1$-$S^o_n$).

In embodiments the angular offset of ring stents may reverse polarity alternately or at a different frequency of reversal, e.g. two aligned ring stents sequentially followed in the axial direction by a ring stent angularly offset in one rotational direction, another ring stent aligned with the said two aligned ring stents, and a next ring stent angularly offset in the opposite rotational direction from the ring stent angularly offset in the one rotational direction.

Alternatively, the plurality of ring stents spaced apart and attached along the length of the tubular member may be configured as at least a first series S of ring stents ($S_1$-$S_n$) and at least one other series $S^{ao}$ of ring stents ($S^{ao}_1$-$S^{ao}_n$) including aligned ring stents ($S^{ao}$), interposed such that at least one ring stent in the first series of ring stents ($S_1$-$S_n$) is located between two ring stents in the at least one other series of ring stents ($S^{ao}_1$-$S^{ao}_n$), and wherein with respect to a first ring stent ($S_1$) having peaks and valleys in the first series of ring stents ($S_1$-$S_n$), the next ring stent ($S_2$) in the first series ($S_1$-$S_n$) has peaks and valleys which are offset angularly with respect to the peaks and valleys of the first ring stent ($S_1$) in the first series ($S_1$-$S_n$), and wherein with respect to a first ring stent ($S^{ao}_1$) in the at least one other series ($S^{ao}_1$-$S^{ao}_n$) the next ring stent ($S^{ao}_2$) in the at least one other series ($S^{ao}_1$-$S^{ao}_n$) has peaks and valleys of which are respectively longitudinally aligned with respect to the corresponding peaks and valleys of the first ring stent ($S^{ao}_1$) in the at least one other series ($S^{ao}_1$-$S^{ao}_n$).

The peaks and valleys of each ring stent in the series of aligned ring stents ($S^{ao}_1$-$S^{ao}_n$) spaced apart and attached along the length of the tubular member may be mutually aligned with the corresponding peaks and valleys of each other ring stent in the series of aligned ring stents ($S^{ao}_1$-$S^{ao}_n$).

At least one circular ring stent may be attached as a terminal stent at the first end of the tubular member, and optionally at least one circular ring stent may be attached as a terminal stent at the second end of the tubular member. Fixation of the terminal stent(s) to tissue may be provided for by provision of eyelets or loops capable of receiving sutures.

The angular offset may lie in the range of 5 to 60 degrees.

The undulating contour of the ring stents in any embodiment may comprise two peaks and two valleys to form a saddle-shaped ring stent. Preferably the peaks and valleys are steeply undulating so that the value H is relatively high, say in the range of 2 to 30 mm.

The inter-stent spacing may have a value which is the product of the height dimension H and a number in the range of 0.3 to 2.

The value of the height dimension H may be different for discrete stents of the plurality of discrete compressible ring stents. Alternatively, the value of the height dimension H may be the same for each of the discrete compressible ring stents of the plurality of discrete compressible ring stents.

In embodiments, at least one ring stent having an undulating contour forming a plurality of alternate peaks and valleys has a height dimension $H_1$ which is different from the height dimension $H_o$ of at least one other ring stent having an undulating contour forming a plurality of alternate peaks and valleys.

In embodiments, the height dimension of respective ring stents having an undulating contour forming a plurality of alternate peaks and valleys may be such that in a first part of the tubular member one or more ring stents having an undulating contour forming a plurality of alternate peaks and valleys may have a height dimension $H_1$, and in a second part of the tubular member one or more ring stents having an undulating contour forming a plurality of alternate peaks and valleys may have a height dimension $H_2$ differing from the height dimension $H_1$ and in an $n^{th}$ part of the tubular member one or more ring stents having an undulating contour forming a plurality of alternate peaks and valleys may have a height dimension $H_n$ differing from the height dimension of ring stents having an undulating contour forming a plurality of alternate peaks and valleys in other parts of the tubular member, where n is a whole number.

Each ring stent may be attached to the tubular member by sutures, adhesive or heat bonding. A plurality of ring stents may be attached to an external surface of the tubular member.

Each ring stent may comprise a shape memory material which may be heat set against the surface of the tubular member.

Further embodiments are defined in the claims hereinafter appearing.

BRIEF DESCRIPTION OF THE DRAWINGS

Several embodiments will now be described by way of illustration with reference to the accompanying drawings.

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 6A and FIG. 6B show side views of the stent graft prosthesis of FIG. 5 from different viewpoints (90° rotation);

DETAILED DESCRIPTION FOR CARRYING OUT THE INVENTION

Figure 1:
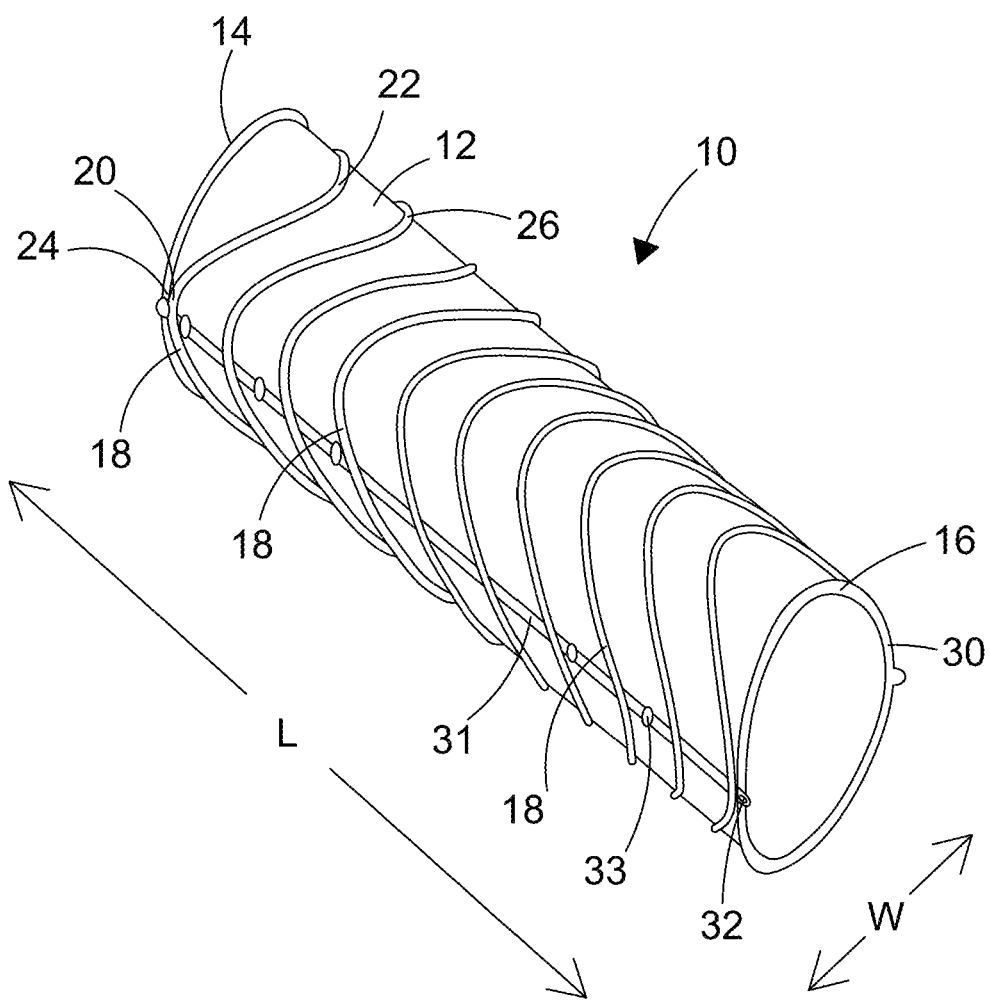
FIG. 1 shows a perspective view of a first embodiment of a stent graft prosthesis as disclosed herein.
Figure 2:
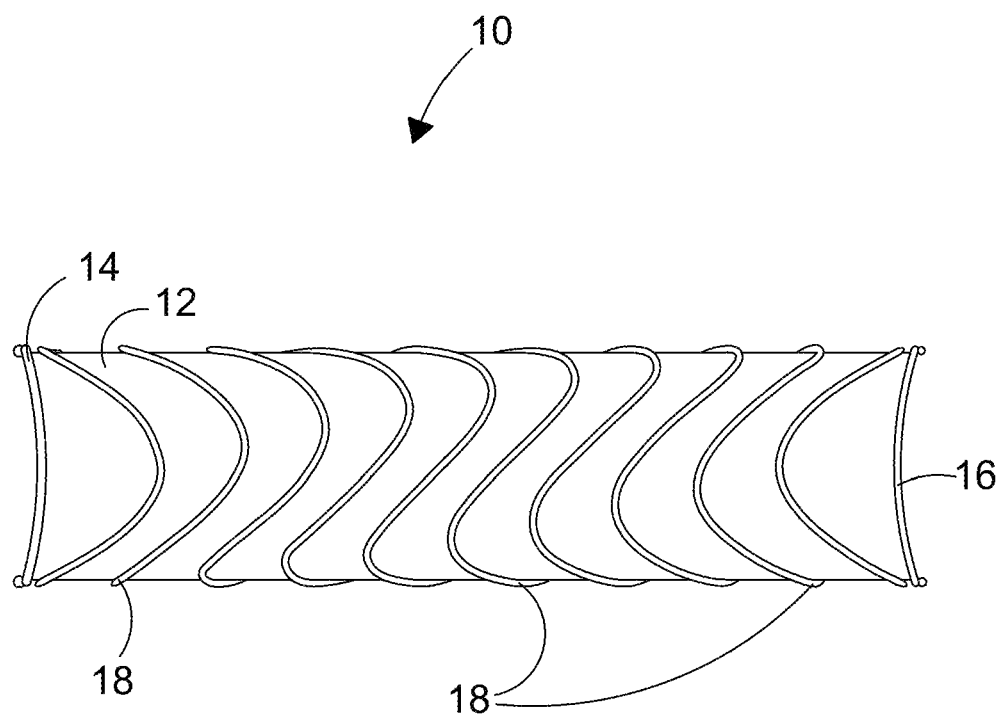
FIG. 2 shows a longitudinal side view of the stent graft prosthesis of FIG. 1 indicating schematically the progressive "spiral" offset of successive ring stents arranged in series along the longitudinal axis of the stent graft prosthesis.
Figure 3A:
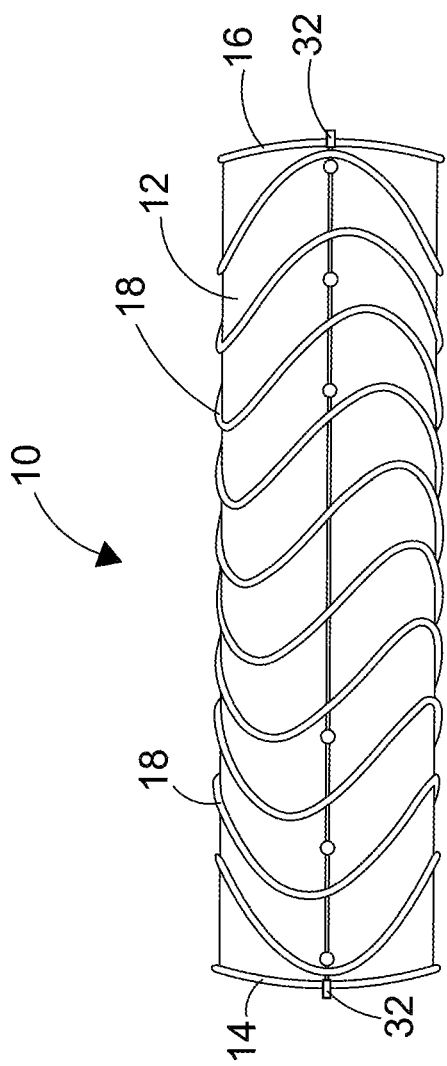
FIG. 3A and FIG. 3B show further side views of the device of FIG. 1 from different viewpoints (90° rotation)
Figure 3B:
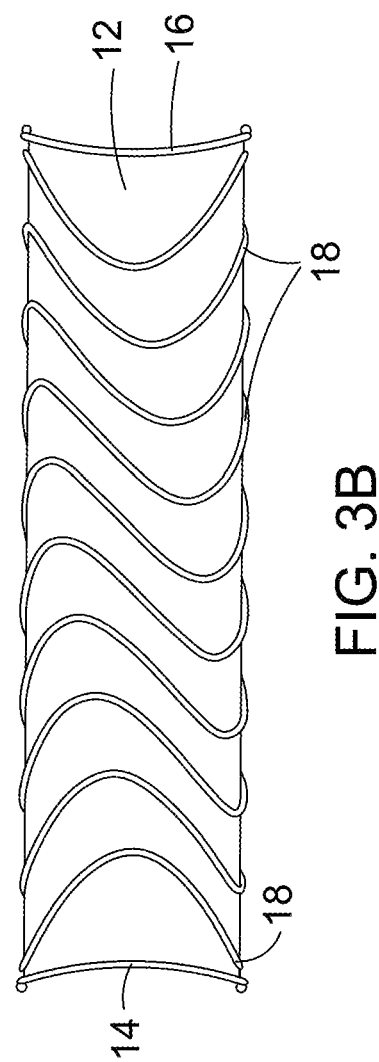

FIGS. 1 to 3B show a first embodiment of a stent graft prosthesis 10. The stent graft prosthesis 10 comprises a tubular member 12 having a length L extending between first and second ends 14, 16, and a lumen width dimension W. The tubular member 12 may be formed from a crimped or uncrimped fabric which may be a knitted or woven fabric of ePTFE, or PTFE, or polyester, or polyethylene or polypropylene and may optionally be coated to reduce friction; discourage clotting or to deliver a pharmaceutical agent. The device 10 also includes a plurality of discrete compressible ring stents 18 spaced apart and attached along the length L of the tubular member 12. Each stent 18 extends around and is attached to an external surface or an internal surface of the tubular member 12 in a direction nonparallel to the length L, and has an undulating contour forming alternating peaks and valleys 20, 22. In the depicted embodiment, the discrete compressible ring stents 18 each extend around and are attached to the outer surface of the tubular member 12.

Each of the ring stents 18 is made of a continuous loop of resilient material such as stainless steel, or a compressible shape memory metal alloy, for example nitinol (a nickel-titanium alloy) or a shape memory high modulus polymer such as polyether ether ketone (PEEK), or any high modulus physiologically benign polymer with shape memory behaviour can be used. The ring stents 18 may be attached to the tubular member 12 by way of sutures, adhesive or heat bonding as appropriate. Each ring stent 18 may be formed from a shape memory material which may be heat set against the external surface of the tubular member 12. In the depicted embodiment, the undulating contour of each ring stent 18 comprises a compressible memory material readily forming two peaks 20 and two valleys 22 to form in use a "saddle-shaped" ring stent. Each ring stent 18 may be formed from a continuous loop of multiple windings of nitinol wire to provide a compressible ring stent capable of adopting a peak and valley "saddle shape".

The peaks and valleys 20, 22 of at least one ring stent 18 are offset angularly with respect to the peaks and valleys of an adjacent equivalent ring stent. In the depicted embodiment the plurality of ring stents 18 are configured as a series of ring stents 18 spaced apart and attached along the length of the tubular member 12. The series includes a first ring stent 24 which has peaks and valleys 20, 22 in the series of ring stents 18. With respect to the first ring stent 24 the next adjacent ring stent 26 in the series has peaks and valleys which are offset angularly with respect to the peaks and valleys of the first ring stent 24, and the peaks and valleys of each successive ring stent 18 in the series are offset angularly with respect to the peaks and valleys of the preceding adjacent stent. In the depicted embodiment, the degree of angular offset is 10 degrees, although the degree of angular offset may lie in the range of 5 to 60 degrees.

In the depicted embodiment, the device 10 includes at least one circular ring stent 30 attached as a terminal stent at the first or second end of the tubular member 12. In the depicted embodiment, the device 10 includes circular ring stents 30 provided at both the first and second ends of the tubular member 14, 16, and an orientation and visualisation aid 31 including a series of spaced apart radiopaque markers 33, extending lengthwise between the circular ring stents 30 along the outer surface of the tubular member 12. The terminal stents 30 illustrated include loop eyelets 32 for securing the tubular form stent graft prosthesis to tissue.

Figure 4:
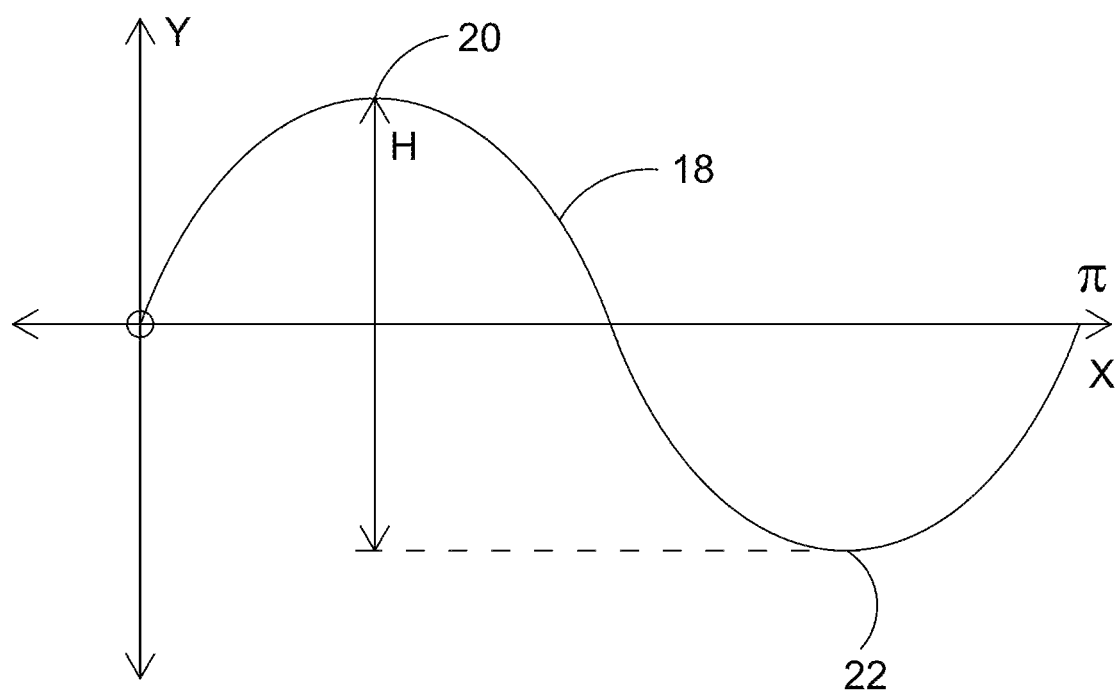
FIG. 4 shows a graph representing the profile of an undulating contour of the stent graft prosthesis of FIG. 1.

Reference is now made to FIG. 4, which illustrates graphically an embodiment profile of the undulating contour of each discrete compressible ring stent 18 plotted on X and Y axes. In the depicted embodiment, the contour includes one peak and one valley and has a substantially sinusoidal profile. Each ring stent 18 has a height dimension H in the range of 2 to 30 mm. The height dimension H is a distance measured along an axis parallel with the length of the tubular member 12 that is determined by measurement between peaks 20 and valleys 22 of the ring stent 18.

The degree of axial displacement between the peaks 20 and the valleys 22 (the "saddle height"), is a function of the original circumference of the ring stent prior to its distortion, relative to the final circumference of a circle within which the distorted (saddle shaped) configuration can be located. Generally the final circumference will be the outer circumference of the graft sleeve to which the stent is to be attached. The percentage oversize of the undistorted inner circumference of the circular stent relative to the outer circumference of the graft sleeve also gives a convenient measure of the saddle shape adopted, and can be calculated as:

$$\text{Oversize \%} = \frac{[\text{Stent inner diameter} - \text{Graft sleeve outer diameter}]}{\text{Graft sleeve outer diameter}} \times 100\%$$

With reference to FIGS. 1 to 3B, the inter-stent spacing may have a value which is the product of the height dimension H and a number in the range of 0.3 to 2. The value of the height dimension H may be different for discrete stents of the plurality of discrete compressible ring stents. Alternatively, the value of the height dimension H may be the same for each of the discrete compressible ring stents of the plurality of discrete compressible ring stents.

Figure 5:
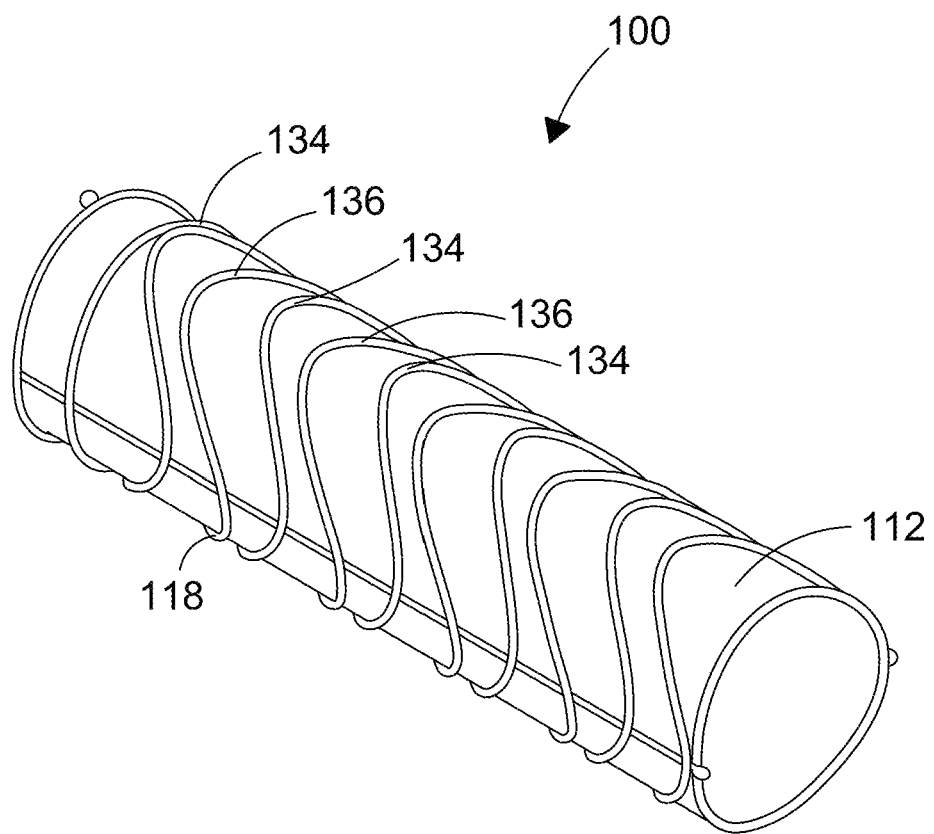
FIG. 5 shows a perspective view of a second embodiment of a stent graft prosthesis as disclosed herein, which comprises first and second series of mutually aligned ring stents arranged along the longitudinal axis of the stent graft prosthesis, wherein the ring stents of each series are interposed between each other such that the respective series as a whole are angularly offset one with respect to the other.

Reference is now made to FIG. 5 and FIGS. 6A-6B, which show a second embodiment of the stent graft prosthesis 100. In the depicted embodiment, the device 100 includes a tubular member 112 as described above and a plurality of discrete compressible ring stents 118 as described above. However, in this embodiment, the plurality of ring stents 118 comprises a first series of aligned ring stents 134 forming a first stent element, and a second series of aligned ring stents 136 interposed between stents of the first series of ring stents and forming a second stent element, and the peaks and valleys of the first series of ring stents are angularly offset from the peaks and valleys of the second series of ring stents, such that the stent elements with respect to each other are mutually offset. Viewed from an alternative standpoint, this embodiment can also be considered as successive ring stents 118 rotationally offset from an axial norm by an angular value that is alternately positive or negative from one ring stent to the next along the length of the tubular member 112.

Figure 7:
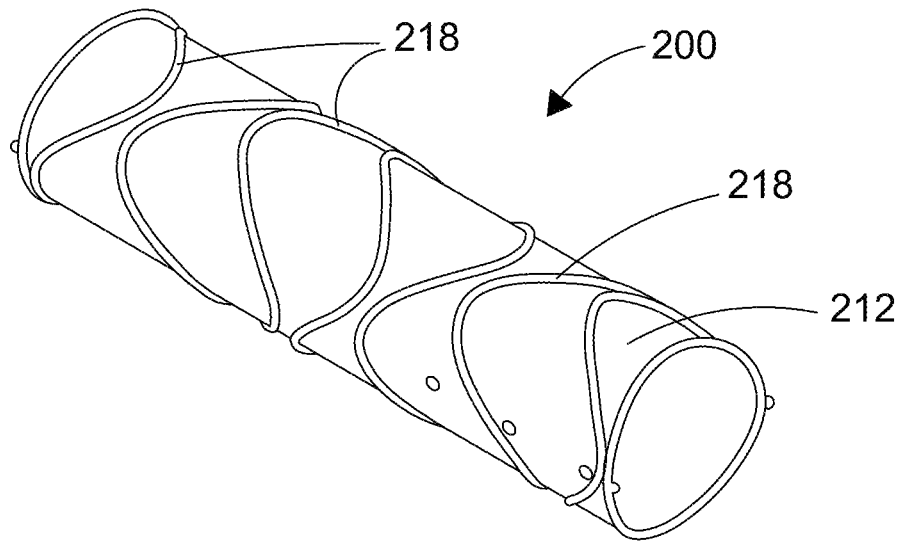
FIG. 7 shows a perspective view of a third embodiment of a stent graft prosthesis as disclosed herein, which has increased spacing between the peaks of successive stents and significantly increased angular offset between successive stents as compared with the stent graft prosthesis of FIG. 1.
Figure 8A:
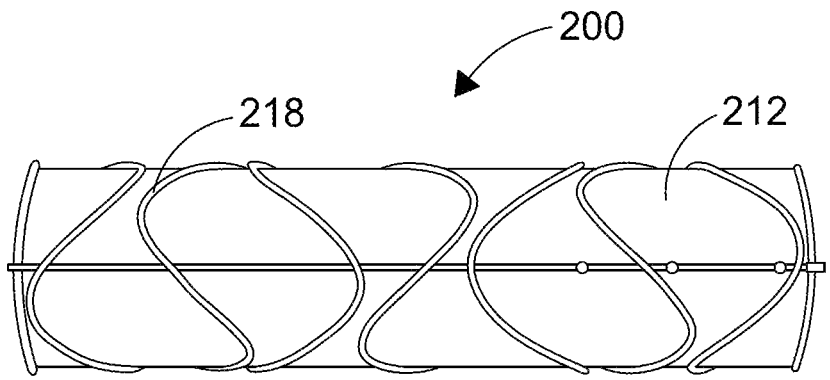
FIG. 8A and FIG. 8B show side views of the device of FIG. 7 from different viewpoints (90° rotation)
Figure 8B:
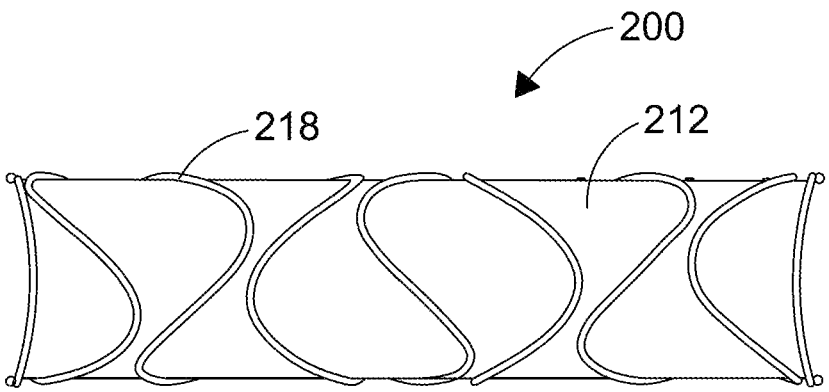

Reference is now made to FIG. 7 and FIGS. 8A-8B, which show a third embodiment of the stent graft prosthesis 200. In the depicted embodiment, the device 200 includes a tubular member 212 as described above and a plurality of discrete compressible ring stents 218 as described above. However, in this embodiment, the degree of angular offset between the peaks and valleys of a first ring stent and the peaks and valleys of a successive ring stent is increased with respect to the first embodiment. In this embodiment, the degree of angular offset is 50 degrees. The spacing between the peak of a first stent and the peak of a successive stent is also greater than in the first embodiment. In this embodiment, the spacing between the peak of a first stent and the peak of a successive stent is 21 mm. In addition, the embodiment includes less discrete compressible ring stents per unit length than the first embodiment. There are seven discrete compressible ring stents provided in the third embodiment depicted in FIG. 7 and FIGS. 8A-8B.

Figure 9:
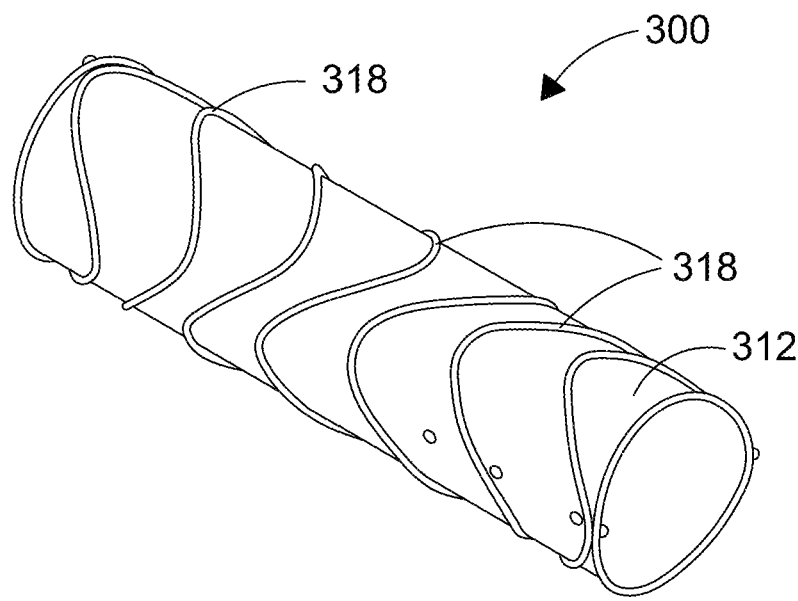
FIG. 9 shows a perspective view of a fourth embodiment of a stent graft prosthesis as disclosed herein, which has less stents per unit length than the stent graft prosthesis of FIG. 1.
Figure 10A:
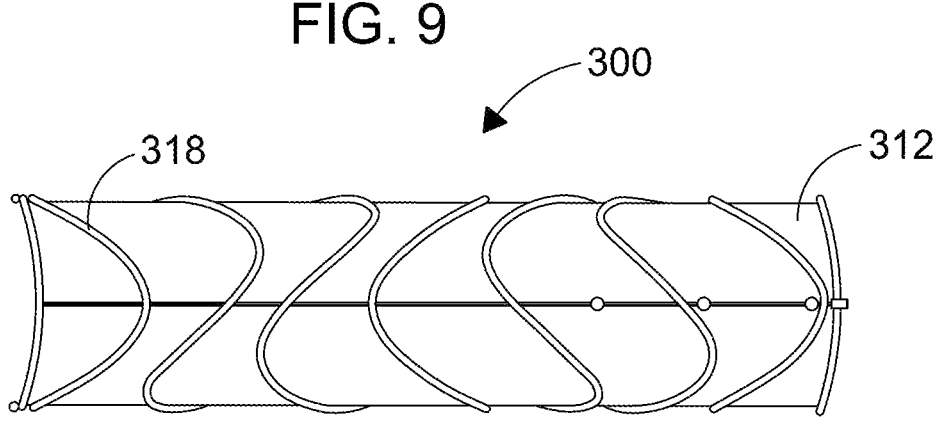
FIG. 10A and FIG. 10B show side views of the device of FIG. 9 from different viewpoints (90° rotation)
Figure 10B:
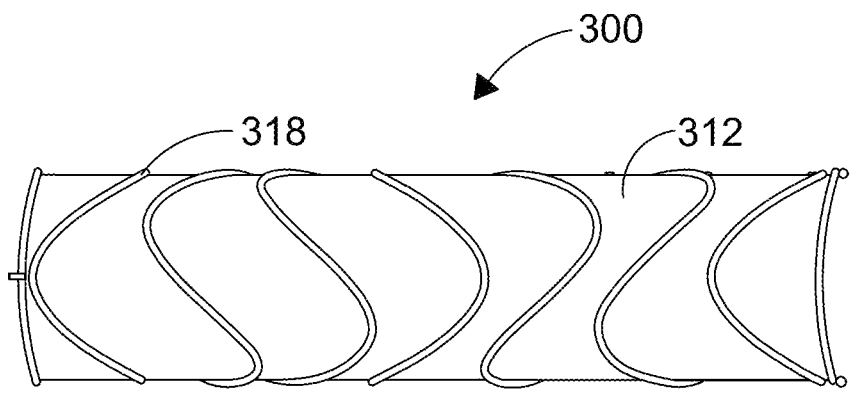

Reference is now made to FIG. 9 and FIGS. 10A-10B, which show a fourth embodiment of the stent graft prosthesis 300. In the depicted embodiment, the device 300 includes a tubular member 312 as described above and a plurality of discrete compressible ring stents 318 as described above. However, in this embodiment the degree of angular offset between the peaks and valleys of a first ring stent and the peaks and valleys of a successive ring stent is increased with respect to the first embodiment. In this embodiment, the degree of angular offset is 30 degrees. The spacing between the peak of a first stent and the peak of a successive stent is also greater than in the first embodiment. In this embodiment, the spacing between the peak of a first stent and the peak of a successive stent is 21 mm. In addition, the embodiment includes less discrete compressible ring stents per unit length than the first embodiment. There are only seven discrete compressible ring stents provided in the fourth embodiment.

Figure 11:
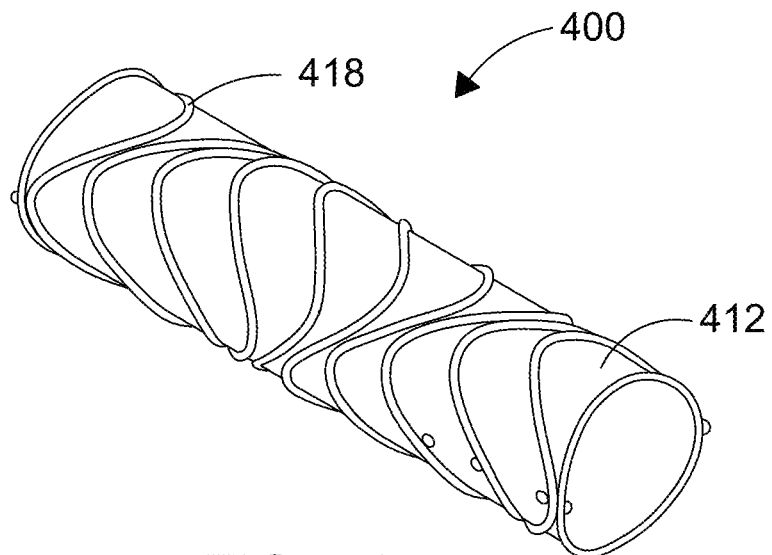
FIG. 11 shows a perspective view of a fifth embodiment of a stent graft prosthesis as disclosed herein, which has an increased angular offset between successive stents with respect to the device of FIG. 1.
Figure 12A:
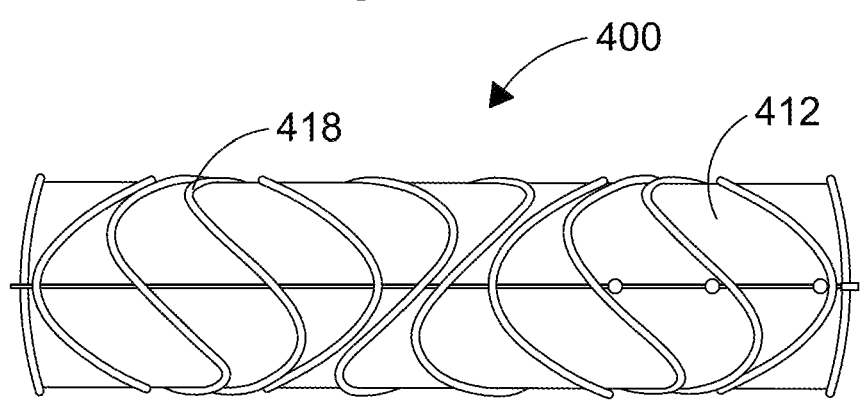
FIG. 12A and FIG. 12B show side views of the device of FIG. 11 from different viewpoints (90° rotation)
Figure 12B:
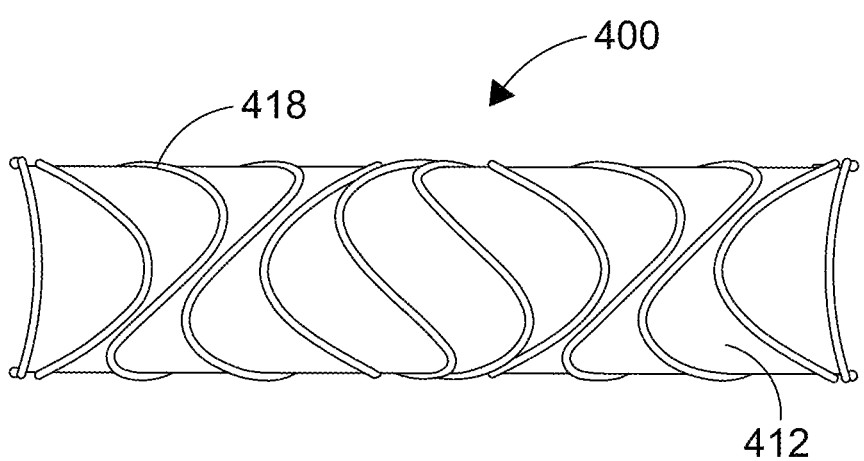

Reference is now made to FIG. 11 and FIGS. 12A-12B, which show a fifth embodiment of the stent graft prosthesis 400. In the depicted embodiment, the device 400 includes a tubular member 412 as described above and a plurality of discrete compressible ring stents 418 as described above. In this embodiment, the spacing between the peak of a first stent and the peak of a successive stent is 14 mm. In this embodiment the degree of angular offset between the peaks and valleys of a first ring stent and the peaks and valleys of a successive ring stent is increased with respect to the first embodiment. In this embodiment, the degree of angular offset is 30 degrees.

Figure 13:
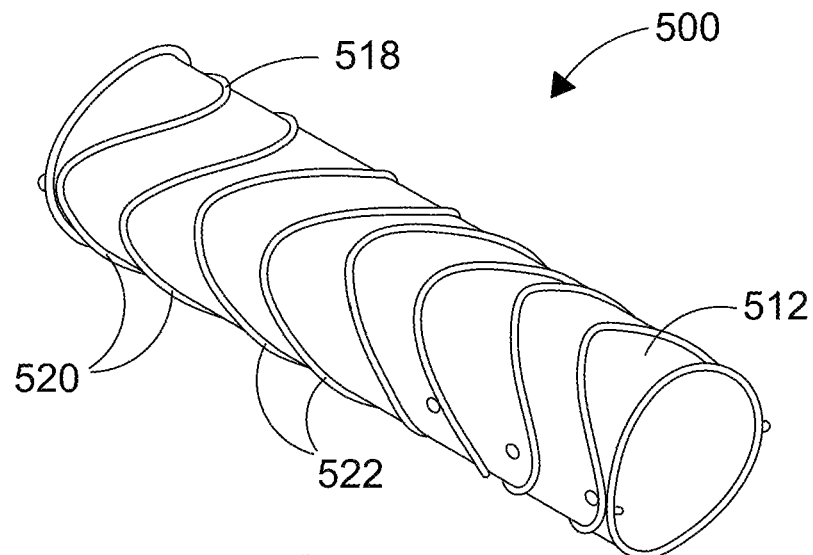
FIG. 13 shows a perspective view of a sixth embodiment of a stent graft prosthesis as disclosed herein, which comprises a series of mutually aligned pairs of adjacent ring stents, wherein the successive pairs of adjacent ring stents are angularly offset from the immediately preceding pair of adjacent ring stents.
Figure 14A:
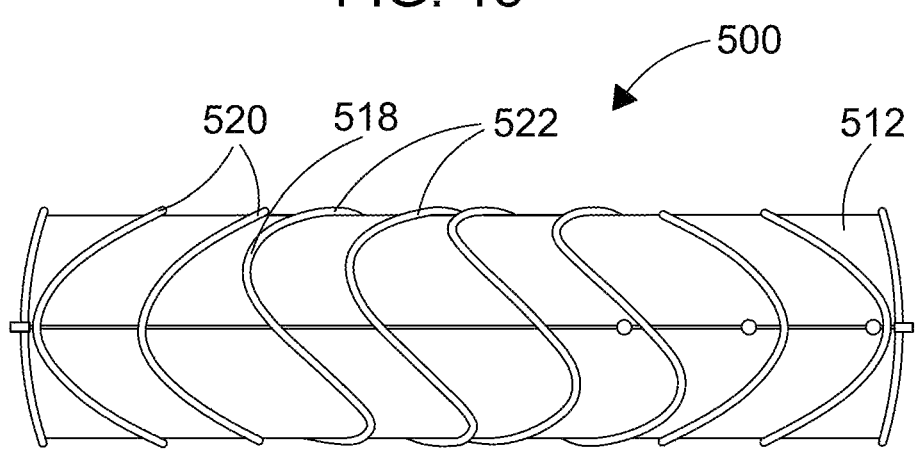
FIG. 14A and FIG. 14B show side views of the device of FIG. 13 from different viewpoints (90° rotation)
Figure 14B:
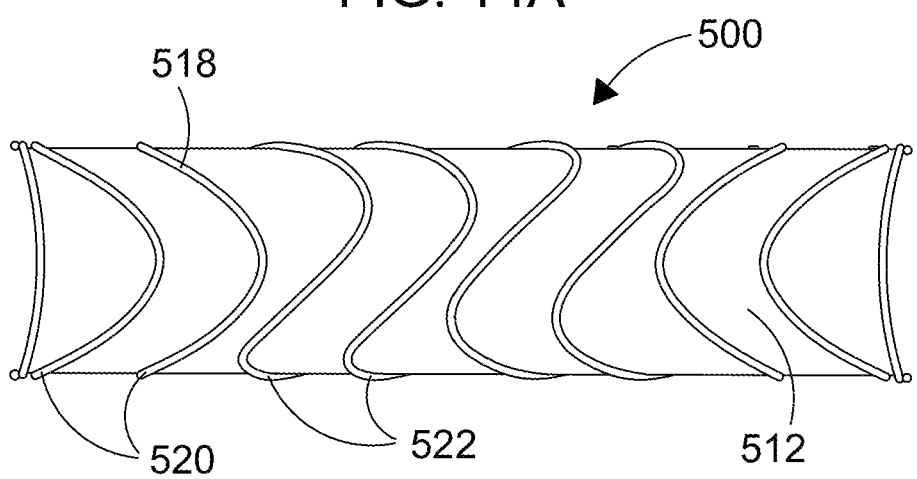

Reference is now made to FIG. 13 and FIGS. 14A-14B, which show a sixth embodiment of the stent graft prosthesis 500. In the depicted embodiment, the device 500 includes a tubular member 512 as described above and a plurality of discrete compressible ring stents 518 as described above. In this embodiment, the ring stents are configured as a series of pairs of mutually aligned adjacent ring stents spaced apart and attached along the length of the tubular member 512. With respect to a first pair 520 having ring stents with peaks and valleys in the series, each of the ring stents of the next adjacent pair 522 in the series of ring stents has peaks and valleys which are offset angularly with respect to the peaks and valleys of each of the rings stents of the first pair.

It will be apparent to the person skilled in the art that different arrangements of stents are possible than those described herein without departing from the scope of the invention defined in the appended claims.

The arrangement of ring stents described herein, and illustrated in FIG. 1 for example, provides increased strength (for example column stiffness) to the stent graft prosthesis 10 when compared to existing devices because there is a localised reduction of surface spacing distance between selected points of ring stents on account of the angular offset of the neighbouring ring stents.

The inventor has proven that the arrangement of ring stents described herein provides increased column stiffness by experimentation. The experimental apparatus and procedure will now be described.

Figure 15:
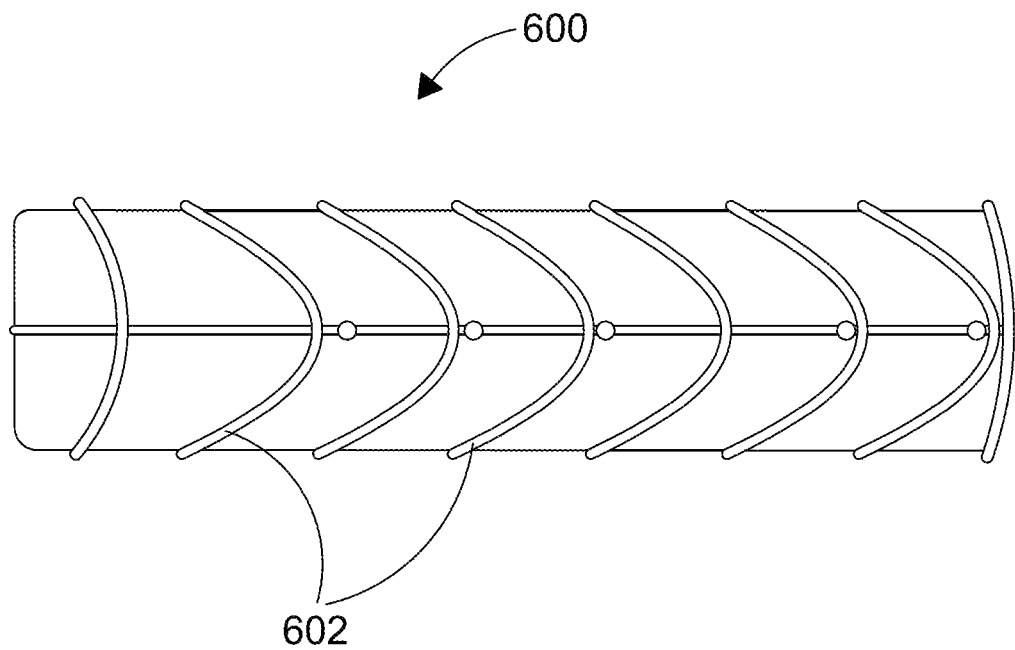
FIG. 15 shows a stent graft according to a prior design, wherein ring stents each having an undulating contour forming a plurality of alternate peaks and valleys, are arranged along the length of the stent graft so as to be axially aligned, peak to peak, valley to valley.

The experimental procedure compared first and second tubular grafts 600, 10. Each of the first and second grafts 600, 10 had a length of substantially 150 mm and a diameter of substantially 40 mm. The first graft 600 corresponded to the graft depicted in FIG. 15. The arrangement of stents 602 of the first graft 600 is typical of prior stent grafts, wherein the individual ring stents are mutually aligned and not angularly offset from one another. The second graft 10 was a graft according to the present invention, and in particular corresponded to the graft depicted in FIGS. 1 to 3B.

Figure 16:
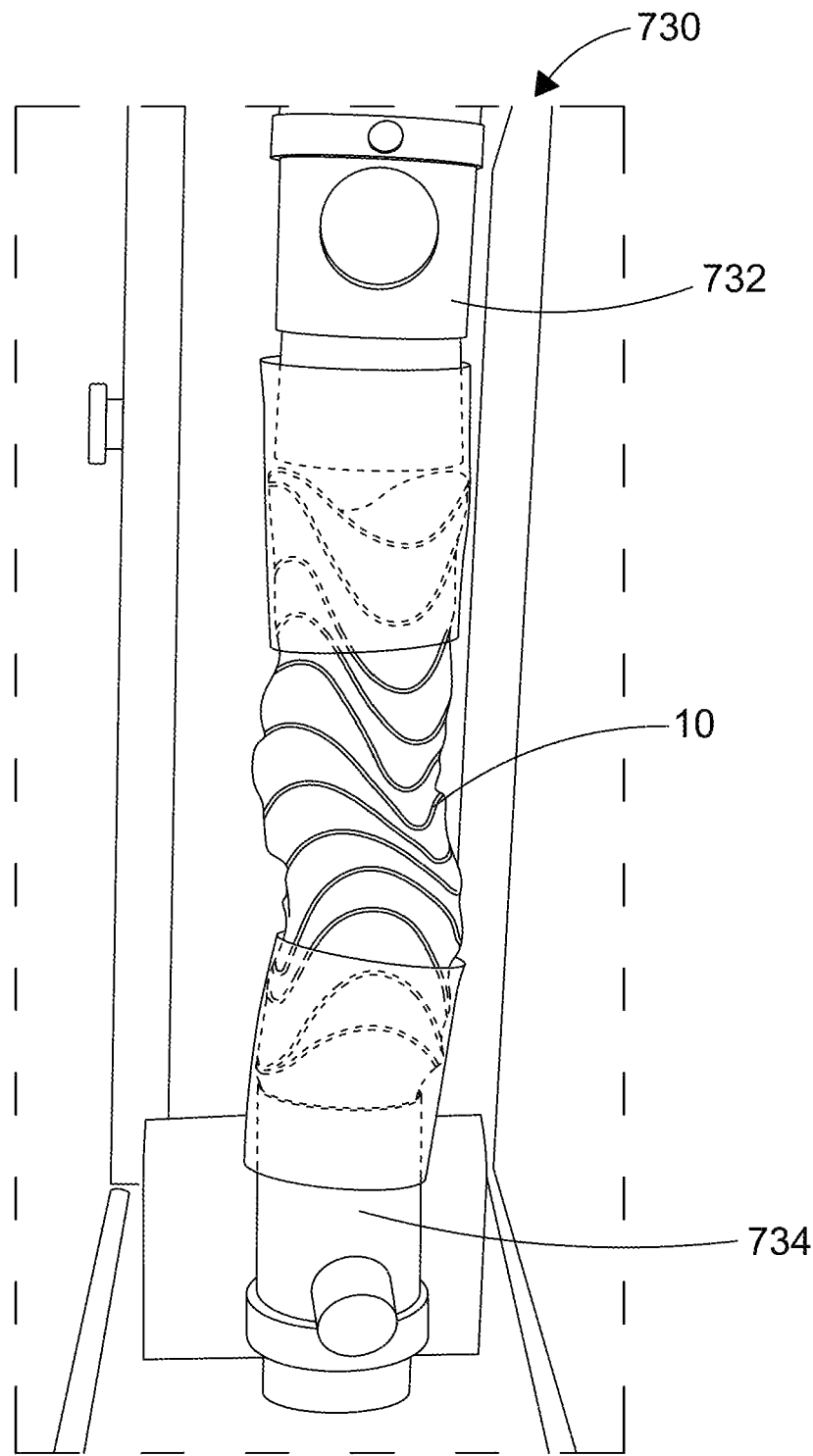
FIG. 16 shows an experimental apparatus arranged to hold and test column stiffness of a stent graft.

Standard compression testing apparatus 730 was used to compare the first and second grafts 600, 10, and the apparatus is depicted in FIG. 16. The apparatus comprises top and bottom anvils 732, 734 that are spaced apart from each other. The top anvil 732 is configured to move axially towards the bottom anvil 734. The apparatus 730 also includes a sensor (not shown) configured to measure force and displacement variables. The displacement variable is the displacement of the top anvil from its starting position, and the force variable is the amount of force required to displace the top anvil from its starting position.

During the experimental procedure, each graft 600, 10 was positioned such that it was sandwiched between the top and bottom anvils 732, 734 and that the length of each graft was aligned with the movement axis of the top anvil 732. This is depicted in FIG. 16, which shows the graft of FIGS. 1-3B sandwiched between the top and bottom anvils 732, 734. After each graft was in position, the top anvil 732 was moved towards the bottom anvil 734 and the force and displacement variables were measured.

Figure 17:
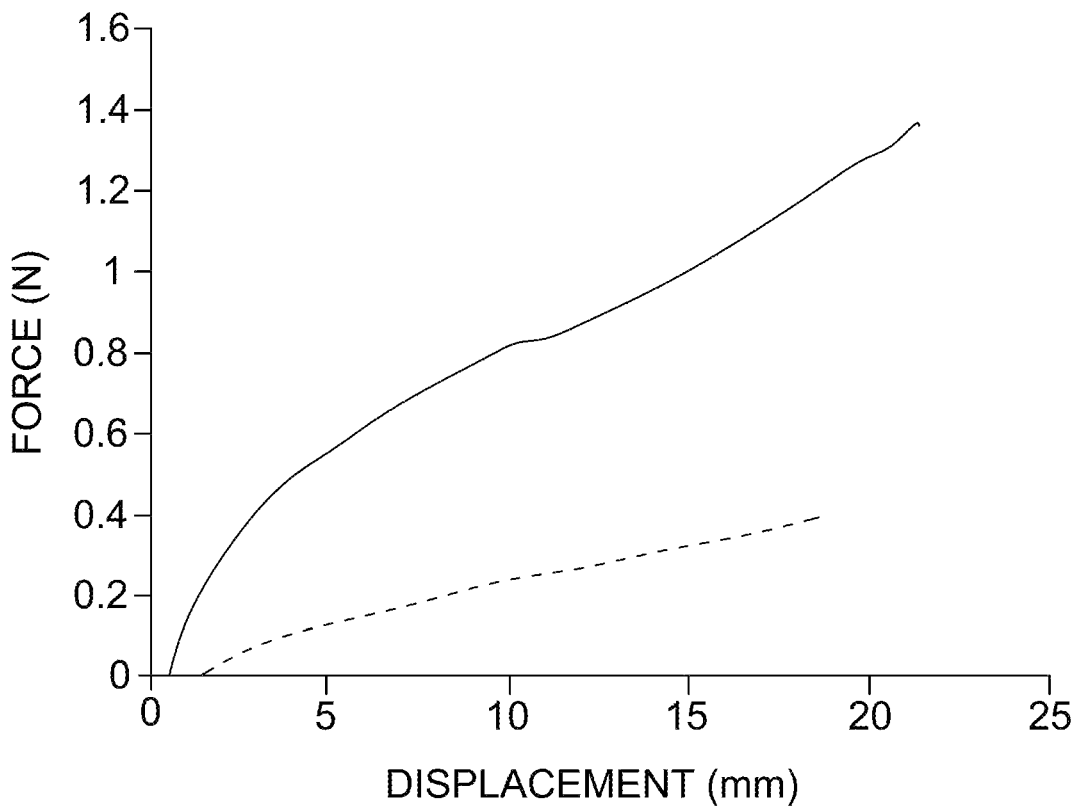
FIG. 17 shows graphically the results of an experiment comparing a stent graft according to the prior design of FIG. 15 and an embodiment as disclosed herein.
Figure 18:
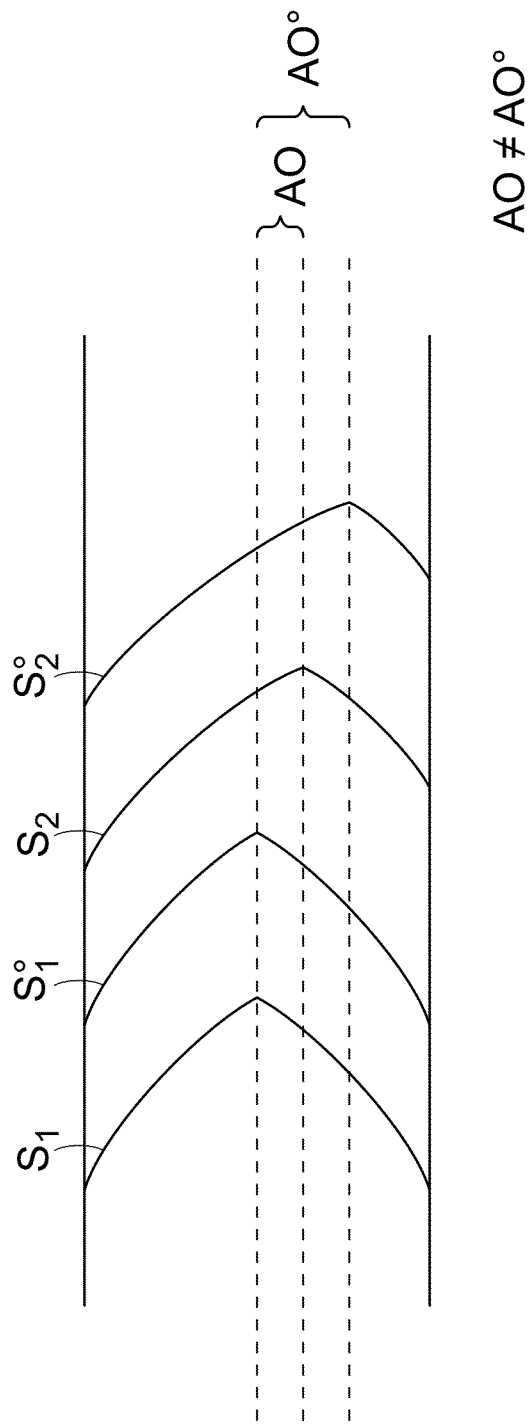
FIG. 18 is a schematic representation of a distribution of compressible ring stents according to another embodiment of the invention, wherein a set of compressible ring stents is interposed with a first set of compressible ring stents, the next compressible ring stent following the first compressible ring stent in each of the series has an angular offset of 5 to 60 degrees, and the angular offset of the first set of compressible ring stents is different than the angular offset of the second set of compressible ring stents.

The results of the experimental procedure are shown in FIG. 17. FIG. 17 shows a graph of force in Newtons (N) against displacement of the top anvil in millimetres (mm) from its starting position for each of the respective grafts. The results for the first graft 600 are depicted by the dotted line and the results for the second graft 10 are depicted by the solid line. As can be seen, the second graft 10 requires a far greater compression force to achieve the same level of displacement when compared to the first graft 600. The experimental procedure therefore clearly shows that the arrangement of stents according to the present invention provides greater column stiffness for a stent graft than the arrangement of stents used in prior stent grafts.

The peaks of the undulating contour of each discrete ring stent urge the fabric of the tubular member 12 outwardly, causing localised 'ovaling' of the tubular member. This effect in conjunction with the angularly offset arrangement of the ring stents allows the stent graft prosthesis 10 to facilitate spiral flow, mimicking fluid flow in the natural vessel, and consequently improves the flow rate in the repaired natural vessel.

The stent graft prosthesis can be inserted into a natural vessel in a patient requiring treatment, the insertion being accomplished using a delivery catheter and, once correctly located at the site requiring treatment, would be deployed by the withdrawal of a delivery sheath of the delivery system. Deployment can be achieved in alternative ways according to existing techniques in the art. Balloon-expandable grafts are caused to expand in diameter by inflation of a balloon associated with the delivery system and located within the lumen of the graft. Self-expandable grafts as disclosed above radially expand upon release from the outer tube. Irrespective of the mode of expansion, once deployed, the stents hold the graft in location by contact with the inner walls of the natural vessel.

Since the stent graft prosthesis will need to be compressed for loading into the catheter and during delivery, in general terms, each stent is formed from the minimum amount of material able to maintain the patency of the sleeve lumen at the required diameter.

Conventional designs of ring stent grafts have focused on alignment of peaks and valleys for compaction/nesting purposes. This invention retains the compaction potential whilst increasing the column strength of the graft.

Each stent can conveniently be positioned externally of the sleeve of the stent graft.

Conveniently, each stent is attached to the graft sleeve by sewing, but any other suitable means of attachment to the sleeve (eg. adhesive or heat bonding) could alternatively be used.

Advantages of embodiments disclosed herein include:
improved column stiffness and strength;
better opportunity for preservation of helical fluid flow characteristics observable in natural vessels;
more control over flexibility of tubular grafts;

potential improvements in modular assembly in situ during a procedure; and improved compaction of tubular graft for delivery purposes.

Modifications and improvements may be incorporated without departing from the scope of the invention, which is defined by the appended claims.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A stent graft prosthesis comprising:
a tubular member having a length dimension extending between a first end of the tubular member and a second end of the tubular member, and a lumen width dimension; and
only two series of discrete compressible ring stents, spaced apart and attached along the length of the tubular member, each compressible ring stent of the two series of compressible ring stents having an undulating contour forming a plurality of alternate peaks and valleys, and a height dimension, each compressible ring stent extending around a surface of the tubular member in a direction non-parallel to the length of the tubular member,
wherein the two series of compressible ring stents that are spaced apart and attached along the length of the tubular member include a first series (S) of the compressible ring stents ($S_1$-$S_n$) and a second series (S°) of the compressible ring stents ($S°_1$-$S°_n$), wherein the compressible ring stents of each series are interposed and alternate between the first and second series and wherein
the respective peaks and valleys of the compressible ring stents of the first series (S) are aligned with each other, the respective peaks and valleys of the compressible ring stents of the second series (S°) are aligned with each other, and each peak of the compressible ring stents of the first series (S) are angularly offset from each peak and valley of the compressible ring stents of the second series (S°), and each valley of the compressible ring stents of the first series (S) are angularly offset from each peak and valley of the compressible ring stents of the second series (S°), and
each compressible ring stent is longitudinally spaced from a directly adjacent compressible ring stent such that an inter-stent spacing is defined between peaks of directly adjacent compressible ring stents, and the inter-stent spacing is the same between the first and second ends of the tubular member.

2. The stent graft prosthesis of claim 1, wherein at least one compressible ring stent is attached as a terminal stent at the first end of the tubular member, and at least one compressible ring stent is attached as a terminal stent at the second end of the tubular member.

3. The stent graft prosthesis of claim 1, wherein the undulating contour of the compressible ring stents comprises two peaks and two valleys to form a saddle-shaped compressible ring stent.

4. The stent graft prosthesis of claim 1, wherein each compressible ring stent is attached to the tubular member by at least one of sutures, adhesive or heat bonding.

5. The stent graft prosthesis of claim 1, wherein at least one compressible ring stent is attached to an external surface of the tubular member.

6. The stent graft prosthesis of claim 1, wherein at least one compressible ring stent is attached to an internal surface of the tubular member.

7. The stent graft prosthesis of claim 1, wherein each compressible ring stent comprises a shape memory material which may be heat set.

8. The stent graft prosthesis of claim 1, wherein each compressible ring stent has a height dimension (H) in the range of 2 to 30 mm, said height dimension being a distance measured along a longitudinal axis aligned with the length of the tubular member determined by measurement between compressible ring stent peaks and compressible ring stent valleys of a compressible ring stent.

9. The stent graft prosthesis of claim 8, wherein a maximum inter-stent spacing dimension (Ax) between the spaced-apart compressible ring stents has a value which is a product of a height dimension ($H_o$) and a number in the range of 0.3 to 2.

10. The stent graft prosthesis of claim 8, wherein at least one compressible ring stent having an undulating contour forming a plurality of alternate peaks and valleys has a height dimension ($H_1$) which is different from the height dimension ($H_o$) of at least one other compressible ring stent having an undulating contour forming a plurality of alternate peaks and valleys.

11. The stent graft prosthesis of claim 8, wherein the value of the height dimension (H) is the same for each discrete compressible ring stent.

12. The stent graft prosthesis of claim 1, wherein at least one of the two series of compressible ring stents have a sinusoidal profile.

13. The stent graft prosthesis of claim 1, wherein the tubular member includes a terminal stent at the first end of the tubular member, the terminal stent includes a loop eyelet.

14. The stent graft prosthesis of claim 1, wherein the angular offset between peaks of the compressible ring stents of the first series and peaks of the compressible ring stents of the second series is within a range of 5 to 60 degrees.

* * * * *